US009848811B2

(12) United States Patent
Yasumura et al.

(10) Patent No.: US 9,848,811 B2
(45) Date of Patent: Dec. 26, 2017

(54) COGNITIVE FUNCTION TESTING SYSTEM, COGNITIVE FUNCTION ESTIMATION SYSTEM, COGNITIVE FUNCTION TESTING METHOD, AND COGNITIVE FUNCTION ESTIMATION METHOD

(71) Applicant: NATIONAL CENTER OF NEUROLOGY AND PSYCHIATRY, Kodaira-shi, Tokyo (JP)

(72) Inventors: Akira Yasumura, Kodaira (JP); Masumi Inagaki, Misato (JP)

(73) Assignee: NATIONAL CENTER OF NEUROLOGY AND PSYCHIATRY, Tokyo (JP)

( * ) Notice: Subject to any disclaimer, the term of this patent is extended or adjusted under 35 U.S.C. 154(b) by 826 days.

(21) Appl. No.: 14/374,048

(22) PCT Filed: Jan. 22, 2013

(86) PCT No.: PCT/JP2013/051187
§ 371 (c)(1),
(2) Date: Jul. 23, 2014

(87) PCT Pub. No.: WO2013/111746
PCT Pub. Date: Aug. 1, 2013

(65) Prior Publication Data
US 2015/0119731 A1 Apr. 30, 2015

(30) Foreign Application Priority Data
Jan. 26, 2012 (JP) .................................. 2012-014531

(51) Int. Cl.
*A61B 5/0476* (2006.01)
*A61B 5/0484* (2006.01)
(Continued)

(52) U.S. Cl.
CPC ............ *A61B 5/168* (2013.01); *A61B 5/0476* (2013.01); *A61B 5/04842* (2013.01); *A61B 5/026* (2013.01);
(Continued)

(58) Field of Classification Search
CPC ......... A61B 5/168; A61B 5/026; A61B 5/165; A61B 5/167; A61B 5/0476; A61B 5/0484; A61B 5/04842
(Continued)

(56) References Cited

U.S. PATENT DOCUMENTS 5,326,270 A * 7/1994 Ostby ...................... G09B 7/04
434/118
6,416,472 B1 * 7/2002 Cady ........................ A61B 5/16
128/920

(Continued)

FOREIGN PATENT DOCUMENTS

| JP | A-2002-112981 | 4/2002 |
|---|---|---|
| JP | A-2006-218065 | 8/2006 |
| WO | WO 2009/148069 A1 | 12/2009 |

OTHER PUBLICATIONS

Ikeda et al., "Features of Stroop/Reverse-Stroop Interference in Two Ways of Reaction," *Committee of Publication of Bulletin of Tokyo Gakugei University*, 2008, pp. 231-235 (with translation).
(Continued)

*Primary Examiner* — Navin Natnithithadha
(74) *Attorney, Agent, or Firm* — Oliff PLC

(57) ABSTRACT

Provided is a cognitive function testing system capable of efficiently and objectively measuring cognitive functions related to, for example, ADHD and easily collecting detailed data. In addition, a cognitive function estimation system is provided to enable estimating and determining the probability of an individual having a disorder such as ADHD after the cognitive functions related to, for example, ADHD have been efficiently and objectively measured. In contrast to the
(Continued)

conventional Stroop interference test that uses paper, one problem is displayed on one screen, and not only the correctness result of the problem for the test subject, but also coordinate information for when the test subject responds by manipulating a touch panel display, are recorded in a problem answer table. Furthermore, an estimation calculation based on a learning algorithm can be used to estimate the degree of cognitive function of the test subject.

12 Claims, 15 Drawing Sheets

(51) Int. Cl.
  *A61B 5/16* (2006.01)
  *A61B 5/026* (2006.01)
(52) U.S. Cl.
  CPC ............. *A61B 5/0484* (2013.01); *A61B 5/165* (2013.01); *A61B 5/167* (2013.01)
(58) Field of Classification Search
  USPC .................................................. 600/544, 545
  See application file for complete search history.

(56) References Cited

U.S. PATENT DOCUMENTS

| | | | | |
|---|---|---|---|---|
| 7,294,107 B2* | 11/2007 | Simon | ...................... | A61B 5/16 434/236 |
| 8,740,623 B2* | 6/2014 | Walker | ..................... | G09B 1/36 434/236 |
| 2002/0072859 A1* | 6/2002 | Kajimoto | ............... | A61B 5/162 702/19 |
| 2005/0273017 A1* | 12/2005 | Gordon | .................. | A61B 5/048 600/544 |
| 2007/0117073 A1* | 5/2007 | Walker | ..................... | G09B 1/36 434/236 |
| 2007/0166675 A1* | 7/2007 | Atkins | ..................... | G09B 5/06 434/236 |
| 2007/0166676 A1* | 7/2007 | Bird | ......................... | G09B 7/04 434/236 |
| 2011/0082677 A1* | 4/2011 | Kawasaki | ................ | A61B 5/16 703/11 |
| 2013/0331727 A1* | 12/2013 | Zhang | .................. | A61B 5/0476 600/544 |
| 2016/0007905 A1* | 1/2016 | Milner | ................ | G06F 19/3431 434/262 |

OTHER PUBLICATIONS

Song et al., "An Asymmetric Stroop/Reverse-Stroop Interference Phenomenon in ADHD," *Journal of Attention Disorders*, 2010, vol. 15, No. 6, pp. 499-505.

International Search Report issued in International Application No. PCT/JP2013/051187 dated Mar. 19, 2013.

* cited by examiner

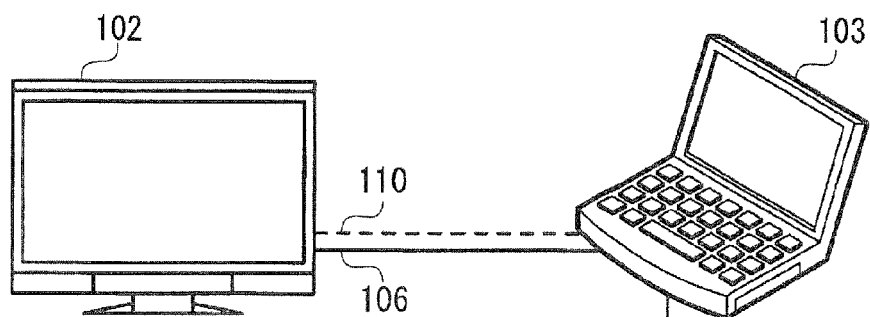
FIG. 1A
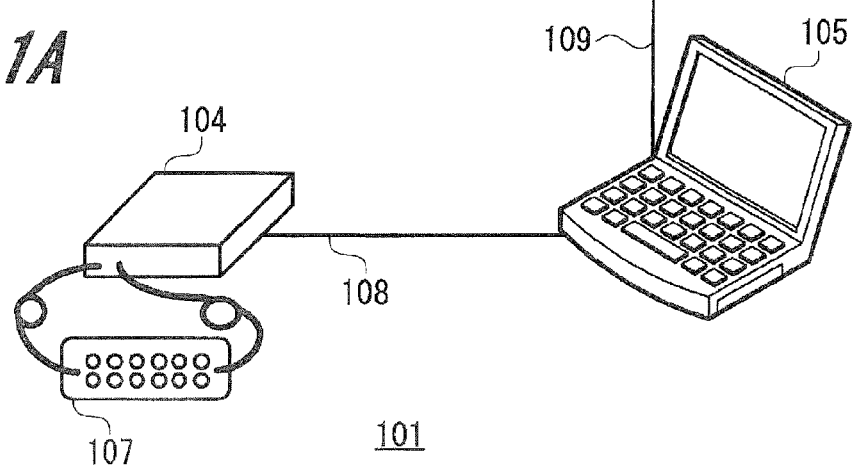
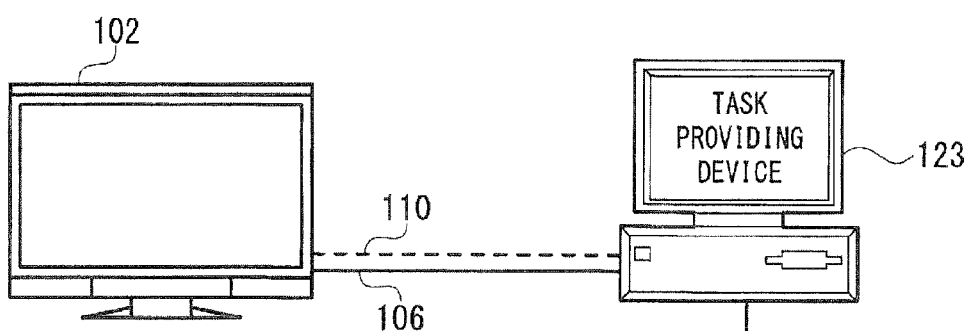
FIG. 1B
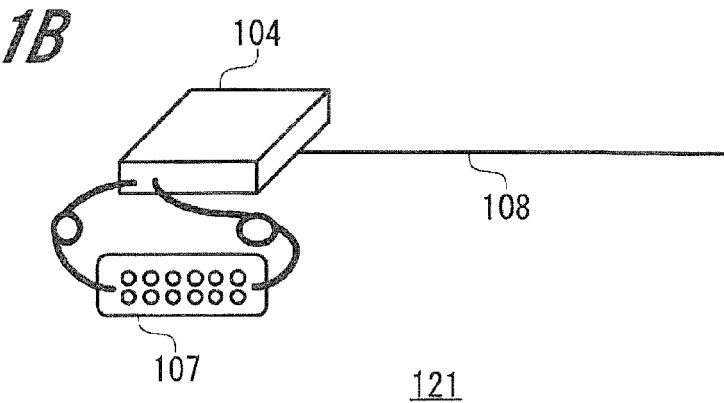

FIG. 8A
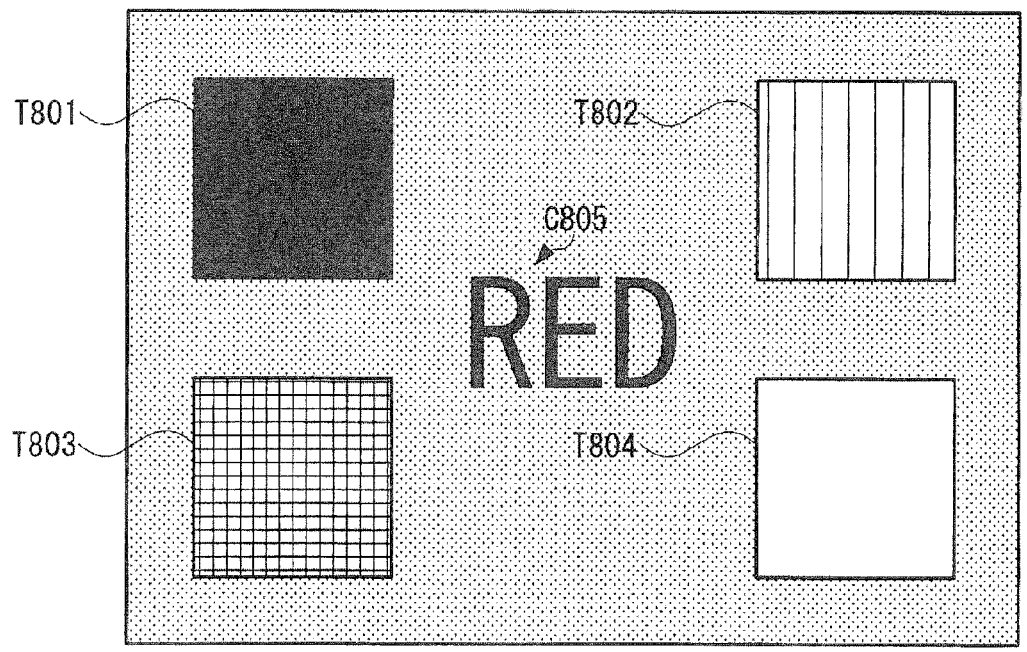
FIG. 8B
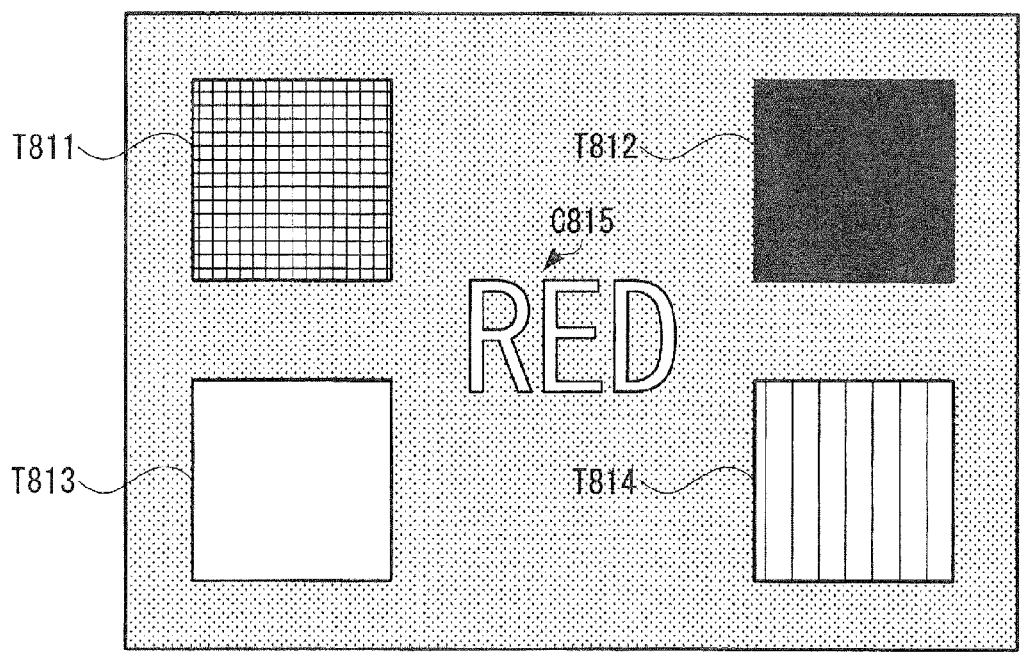
 RED   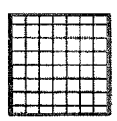 YELLOW   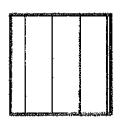 GREEN   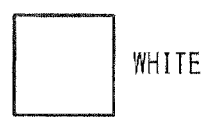 WHITE

FIG. 10

| | Task | TDC | ASD | ADHD | F, p value |
|---|---|---|---|---|---|
| INTERFERENCE RATE (%) | STROOP | 8.30 (11.13) | 10.82 (9.81) | 12.94 (15.76) | 0.44, 0.646 |
| | REVERSE STROOP | 8.94 (4.11) | 8.35 (8.61) | 17.87 (9.15)** | 5.83, 0.007 |
| NUMBER OF WRONG ANSWERS (n) | STROOP | 0.433 (0.56) | 0.50 (0.50) | 0.75 (0.63) | 0.98, 0.385 |
| | REVERSE STROOP | 0.33 (0.59) | 0.41 (0.58) | 0.95 (0.64)* | 3.45, 0.043 |
| RESPONSE TIME (s) | STROOP | 1.73 (0.40) | 1.94 (0.49) | 1.99 (0.63) | 1.07, 0.355 |
| | REVERSE STROOP | 1.32 (0.19) | 1.36 (0.36) | 1.43 (0.39) | 0.41, 0.664 |
| RATE OF CORRECT ANSWERS (%) | STROOP | 96.4 (5.14) | 95.32 (5.96) | 93.28 (6.48) | 0.90, 0.417 |
| | REVERSE STROOP | 98.13 (3.28) | 97.29 (4.02) | 93.58 (5.35)* | 3.80, 0.033 |

FIG. 13A
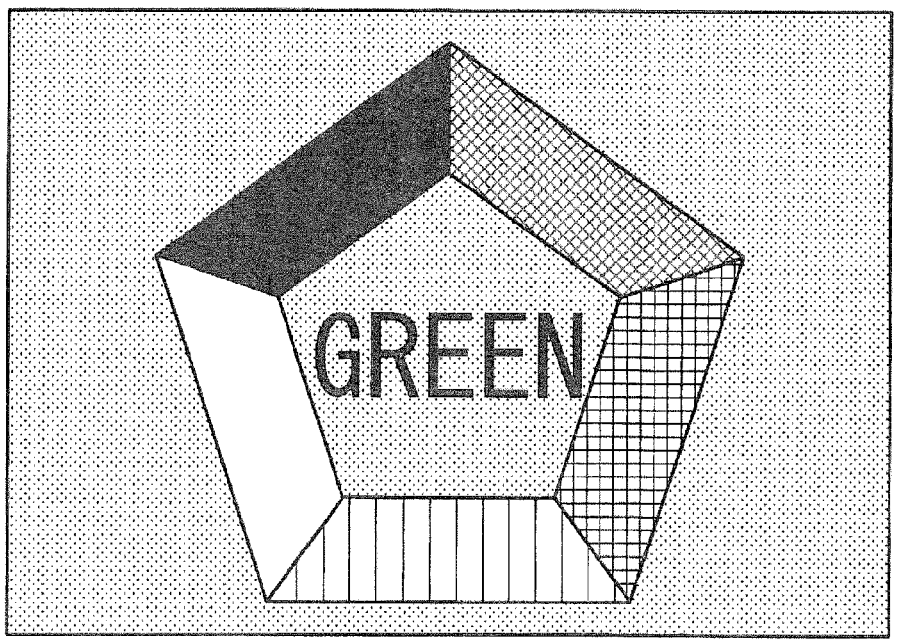
FIG. 13B
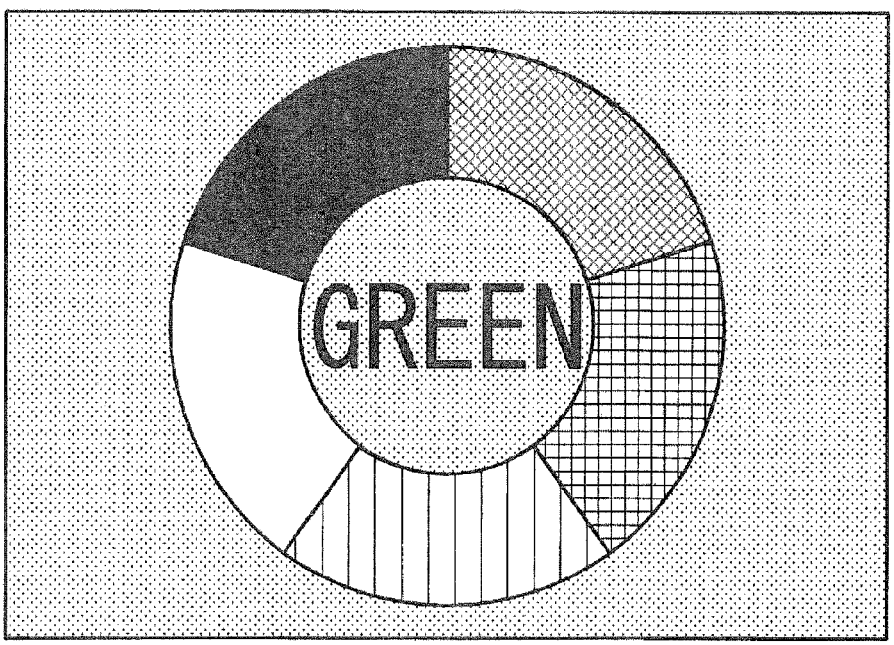
 RED 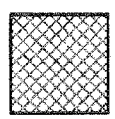 BLUE 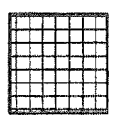 YELLOW  GREEN WHITE

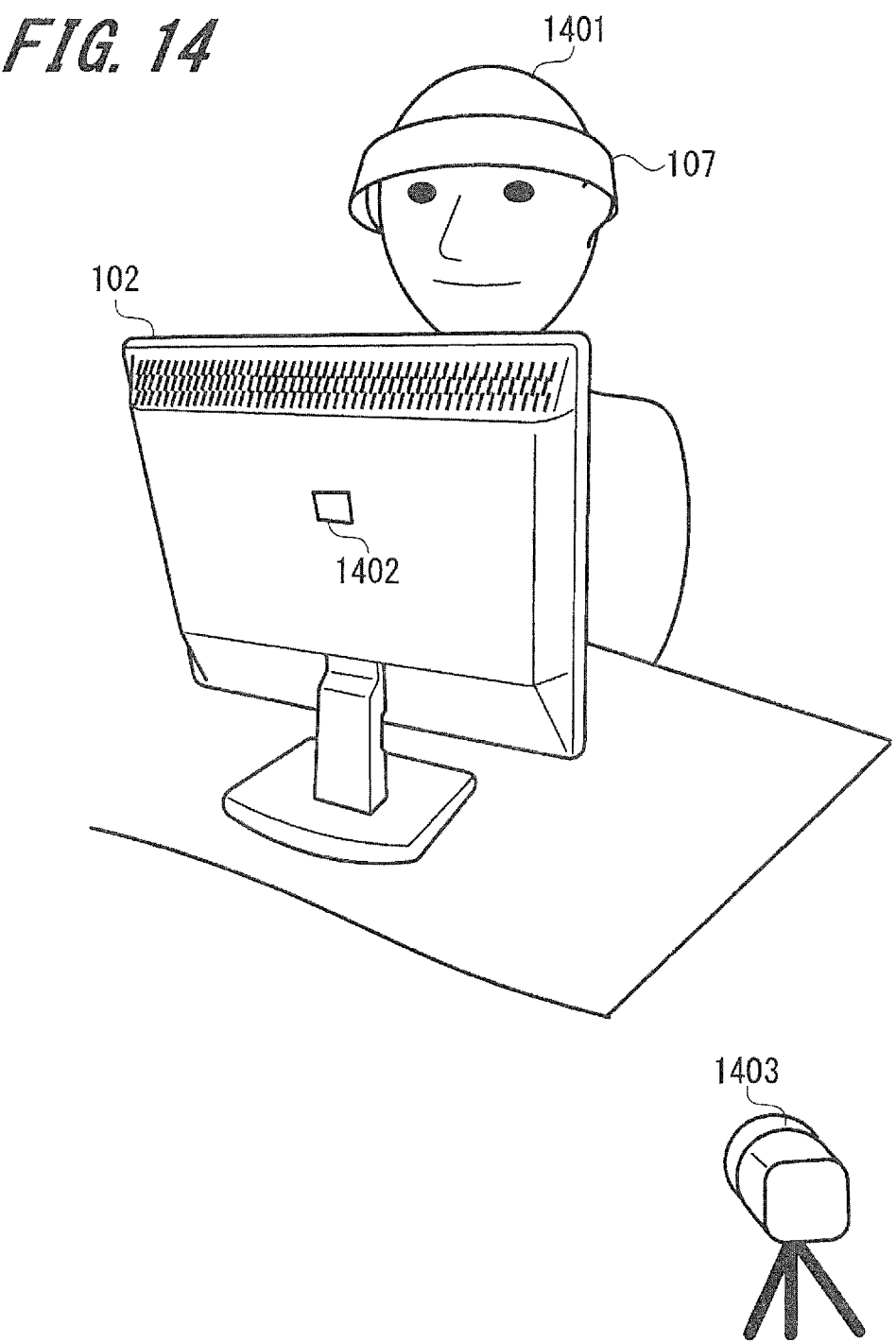

COGNITIVE FUNCTION TESTING SYSTEM, COGNITIVE FUNCTION ESTIMATION SYSTEM, COGNITIVE FUNCTION TESTING METHOD, AND COGNITIVE FUNCTION ESTIMATION METHOD

TECHNICAL FIELD

The present invention relates to a technique preferably applicable to a cognitive function testing system, a cognitive function estimation system, a cognitive function testing method, and a cognitive function estimation method.

More specifically, the invention relates to a cognitive function testing system which is capable of efficiently and objectively measuring data related to a cognitive function of a person, a cognitive function estimation system configured to estimate, after having measured the data related to the cognitive function of a person, the degree of the cognitive function, and a method of the both.

BACKGROUND ART

Attention Deficit/Hyperactivity Disorder, AD/HD for short in the following description, refers to developmental disorder or behavioral disorder characterized by symptoms such as hyperactivity, impulsivity, carelessness, or the like. ADHD, which disturbs group behavior, is mainly observed among children and the symptoms usually improve as they come of age, but it is said that the symptoms may remain among some of the adults.

Although studies of ADHD are underway across the world, there are many issues that are yet to be unveiled such as the cause and mechanism of onset, relevance with other psychiatric disorder, effective therapeutic methods, and the like. Being a juristic person engaged in the field of clinical psychiatry, the applicant of the invention has been promoting studies of ADHD while working on treatment of ADHD patients.

Meanwhile, there are shown Patent Literature 1, Patent Literature 2, Non-patent Literature 1 and Non-patent Literature 2, as prior art documents considered relevant to the present invention.

CITATION LIST

Patent Literature

PTL 1: Japanese Patent Laid-Open No. 2002-112981
PTL 2: Re-publication of Japanese Patent Laid-Open No. 2009/148069

Non Patent Literature

NPL 1: Yoshifumi IKEDA, Shogo HIRATA, Hideyuki OKUIZUMI, "Features of Stroop/reverse Stroop Interference in two ways of Reaction", Committee of Publication of Bulletin of Tokyo Gakugei University (Retreived on Jan. 19, 2012), Internet URL: http://ir.u-gakugei.ac.jp/bitstream/2309/95639/1/18804306_60_24.pdf
NPL 2: Yongning Song, Yuji Hakoda "An Asymmetric Stroop/reverse Stroop Interference Phenomenon in ADHD", Journal of Attention Disorders 2011 15: 499 originally published online 2 Aug. 2010

SUMMARY OF INVENTION

Technical Problem

There is no reliable method established for objectively diagnosing whether or not a subject has ADHD. In view of the status quo, several studies have been reported for determining ADHD.

Non-patent literature 1 is a study report regarding the relevance of ADHD to "Stroop interference" and "reverse Stroop interference".

In addition, Non-patent literature 2 suggests that "the characteristics of ADHD obstacles are more outstanding in a reverse Stroop task than a Stroop task".

Stroop interference is defined as "a phenomenon that occurs in the case of answering the color of the word when the meaning of a written word is different from the color of the word".

Now, identical figures are printed on a paper sheet or the like with a plurality of colors such as "red", "green", "yellow", "white" or the like, and a word describing the name of one of the colors is written with that color. For example, there is prepared a printed matter having the word "red" written in red ink. The subject is asked to look at the word on the printed matter and select a figure colored in the same color as the meaning of the word.

Next, identical figures are printed on a paper sheet or the like with a plurality of colors, and a word describing the name of one of the colors are written with a different color. For example, there is prepared a printed matter having the word "red" written in green ink. The subject is asked to look at the word on the printed matter and select a figure colored in the same color as the color of the word. In such a case, the figure colored in the color of the word, for example, green, is the correct answer. This is the Stroop interference test.

Reverse Stroop interference is defined as "a phenomenon that occurs in the case of answering the meaning of the word when the meaning of a written word is different from the color of the word".

Now, identical figures are printed on a paper sheet or the like with a plurality of colors such as "red", "green", "yellow", "white" or the like, and a word describing the name of one of the colors is written with that color. For example, there is prepared a printed matter having the word "red" written in red ink. The subject is asked to look at the word on the printed matter and select a figure colored in the same color as the meaning of the word.

Next, identical figures are printed on a paper sheet or the like with a plurality of colors, and a word describing the name of one of the colors are written with a different color. For example, there is prepared a printed matter having the word "red" written in green ink. The subject is asked to look at the word on the printed matter and select a figure colored in the same color as the meaning of the word. In such a case, the figure colored in the meaning of the word, for example, red, is the correct answer. This is the reverse Stroop interference test.

However, conventionally, tests of Stroop interference and reverse Stroop interference have been performed on paper. In addition, printed matters of the tests have been printed in a manner such that a plurality of color sample questions has been listed on a single sheet, and interference between upper and lower questions has not been negligible.

The present invention has been made in view of the aforementioned problem, and an object of the present invention is to provide a cognitive function testing system and a cognitive function testing method, which are capable of efficiently and objectively measuring a cognitive function related to ADHD or the like and easily collecting detailed data.

In addition, the present invention has been made in view of the aforementioned problem, and another object of the present invention is to provide a cognitive function estimation system and a cognitive function estimation method, which are capable of estimating and determining the possibility that an individual has a disorder such as ADHD, after having efficiently and objectively measured a cognitive function related to ADHD or the like.

Solution to Problem

A cognitive function testing system of the present invention includes, in order to solve the aforementioned problem, a display section capable of displaying a plurality of colors; a position detecting section configured to output coordinate information of a position touched with a subject's finger or a position indicator used by the subject, and configured to form a touch panel display by being combined with the display section; and a task creating section configured to create a task including tiles of a plurality of colors and words indicating colors, for being displayed on the display section. The cognitive function testing system further includes a task answer table recording the task and the coordinate information; and an input/output control section configured to display the task on the display section and record the task and the coordinate information in the task answer table.

Furthermore, the cognitive function testing system of the present invention includes a timer configured to measure elapsed time, in order to solve the aforementioned problem. It is more preferable that the input/output control section records, in the task answer table, a response time from a time when the task is displayed on the display section by using the timer to a time when the position detecting section is operated.

Furthermore, in order to solve the aforementioned problem, it is more preferable that the cognitive function testing system of the present invention includes a brain activity table recording data derived from brain activity of the subject; and a brain activity recording section configured to record, in the brain activity table by a predetermined sampling clock, the data derived from brain activity of the subject and trigger data generated by the input/output control section at a predetermined timing.

Additionally, in order to solve the aforementioned problem, a cognitive function estimation system of the present invention includes a display section capable of displaying a plurality of colors; a position detecting section configured to output coordinate information of a position touched with a subject's finger or a position indicator used by the subject, and configured to form a touch panel display by being combined with the display section; and a task creating section configured to create a task including tiles of a plurality of colors and words indicating colors, for being displayed on the display section. The cognitive function estimation system further has a task answer table recording the task and the coordinate information; and an input/output control section configured to display the task on the display section, record the task and the coordinate information in the task answer table, and estimate the cognitive function of the subject on the basis of the task and the coordinate information recorded in the task answer table.

Furthermore, in order to solve the aforementioned problem, the cognitive function estimation system of the present invention includes a timer configured to measure elapsed time. It is more preferable that the input/output control section records, in the task answer table, a response time from a time when the task is displayed on the display section by using the timer to a time when the position detecting section is operated.

Moreover, in order to solve the aforementioned problem, it is more preferable that the cognitive function estimation system of the present invention includes a brain activity table recording data derived from brain activity of the subject; and a brain activity recording section configured to record, in the brain activity table by a predetermined sampling clock, the data derived from brain activity of the subject and trigger data generated by the input/output control section at a predetermined timing.

Additionally, in order to solve the aforementioned problem, a cognitive function testing method of the present invention performs a task displaying step of creating a task including tiles of a plurality of colors and words indicating colors, and displaying the task on a display section capable of displaying a plurality of colors; and an answer recording step of outputting coordinate information of a position touched with a subject's finger or a position indicator used by the subject, and recording the coordinate information obtained from a position detecting section that forms a touch panel display by being combined with the display section, in a task answer table together with the task. The task displaying step and the answer recording step are repeated during a predetermined time period.

Furthermore, in order to solve the aforementioned problem, it is more preferable that the answer recording step of the cognitive function testing method of the present invention also records, in the task answer table, the elapsed time from a time when the task is displayed on the display section at the task displaying step to a time when the coordinate information is obtained from the position detecting section.

Moreover, in order to solve the aforementioned problem, it is more preferable that the cognitive function testing method of the present invention includes a brain activity recording step of recording data derived from brain activity of the subject in the brain activity table while the repeating step is being performed.

Additionally, in order to solve the aforementioned problem, a cognitive function estimation method of the present invention performs a task displaying step of creating a task including tiles of a plurality of colors and words indicating colors, and displaying the task on a display section capable of displaying a plurality of colors; and an answer recording step of outputting coordinate information of a position touched with a subject's finger or a position indicator used by the subject, and recording the coordinate information obtained from a position detecting section that forms a touch panel display by being combined with the display section, in a task answer table together with the task. In addition, the cognitive function estimation method also performs a repeating step of repeating the task displaying step and the answer recording step during a predetermined time period; and a cognitive function estimating step of estimating the cognitive function of the subject on the basis of the task and the coordinate information, recorded in the task answer table.

Furthermore, in order to solve the aforementioned problem, it is more preferable that the answer recording step of the cognitive function estimation method of the present invention also records, in the task answer table, the elapsed time from a time when the task is displayed on the display section at the task displaying step to a time when the coordinate information is obtained from the position detecting section.

Moreover, in order to solve the aforementioned problem, it is more preferable that the cognitive function estimation method of the present invention includes a brain activity recording step of recording data derived from brain activity of the subject in the brain activity table while the repeating step is being performed, and that the cognitive function estimating step also uses data derived from brain activity of the subject and recorded in the brain activity table, for an estimation calculation of the cognitive function.

Unlike the conventional paper-based Stroop interference test, the cognitive function testing system of the present invention displays one task on one screen and records, in the task answer table, not only the subject's correct or wrong answer to a task but also the coordinate information when the subject performs an answering operation on the touch panel display. Accordingly, the tendency of the subject's answers can be collected in the form of data, and thus there can be provided data very useful for analyzing and considering a large variety of data for various psychiatric disorders besides ADHD.

The addition of an estimation processing function to the cognitive function testing system makes it possible to estimate the level of the cognitive function of the subject.

Advantageous Effects of Invention

According to the present invention, a cognitive function testing system and a cognitive function testing method can be provided, which are capable of efficiently and objectively measuring a cognitive function related to ADHD or the like and easily collecting detailed data.

In addition, according to the present invention, a cognitive function estimation system and a cognitive function estimation method can be provided, which are capable of efficiently and objectively measuring a cognitive function related to ADHD or the like and then estimating and determining the possibility that an individual has a disorder such as ADHD.

BRIEF DESCRIPTION OF DRAWINGS

FIG. 1 is a schematic view illustrating a first example and a second example of a cognitive function testing system which is an exemplary embodiment of the present invention;

FIG. 8 is an exemplary display screen displayed on a touch panel display by the cognitive function testing system of the present embodiment;

FIG. 10 is a table indicating the result of the test performed by the cognitive function testing system on a group of typically developed children, ASD children, and ADHD children;

FIG. 13 is an exemplary display screen when using five colors on the display screen, which is one of applications of the present embodiment;

FIG. 14 is a schematic view illustrating a scene of photographing the subject and the cognitive function testing system by using a video camera;

DESCRIPTION OF EMBODIMENTS

[Cognitive Function Testing System: Overall System]

Figure 2:
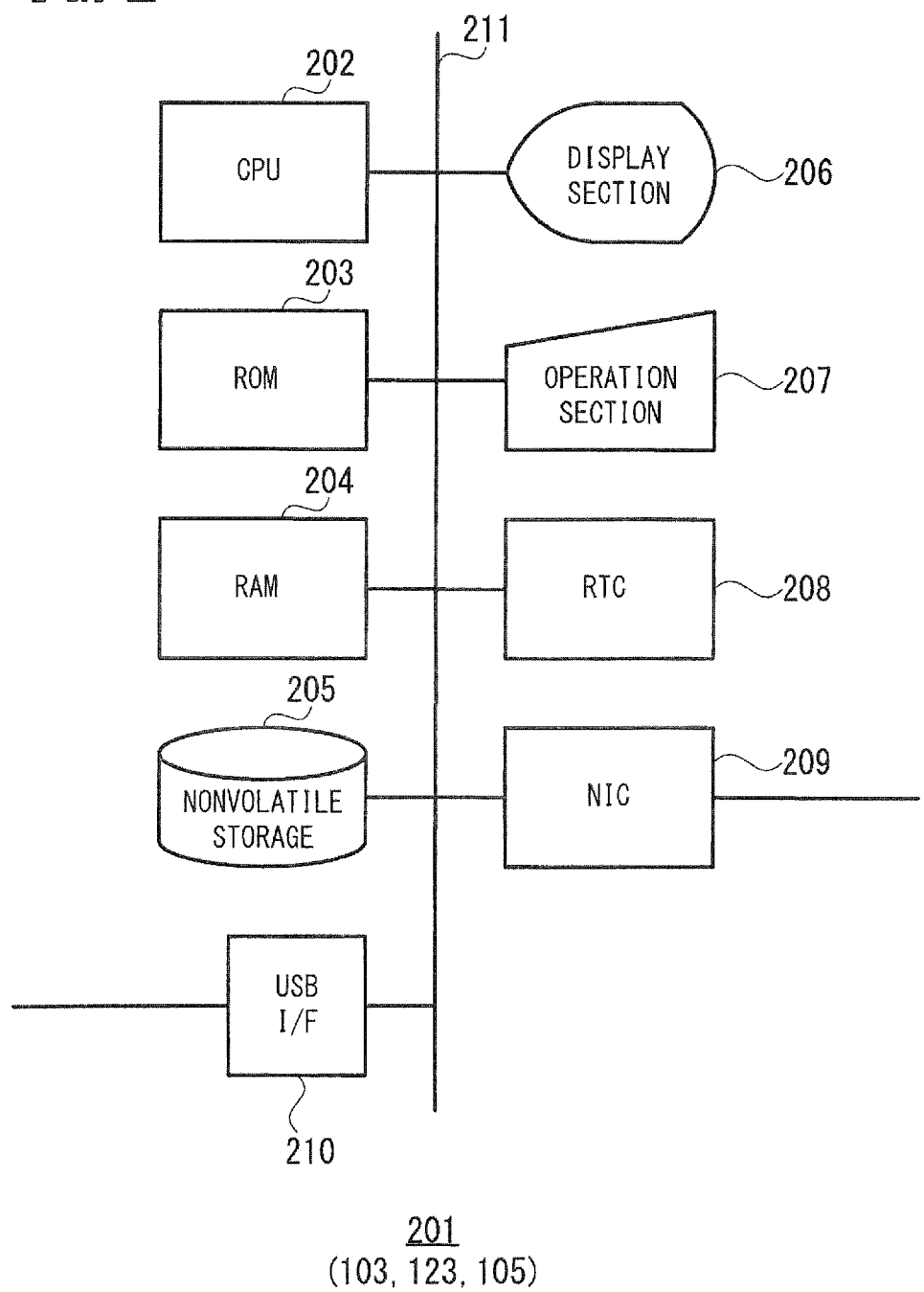
FIG. 2 is a block diagram illustrating a hardware configuration of a personal computer.

FIGS. 1A and B are schematic views of a cognitive function testing system which is an example of the first embodiment of the present invention.

First, a cognitive function testing system 101 illustrated in FIG. 1A will be described.

The recognition function testing system 101 includes a touch panel display 102, a task providing device 103, a brain blood flow measuring device 104, and a brain activity recording device 105.

The touch panel display 102 is configured by combining a touch panel (position detecting device) using a transparent electrode, with a well-known liquid crystal display. The touch panel outputs information of the X coordinate and the Y-coordinate of a position touched by a finger. The well-known resistance membrane method, electrostatic method, or the like may be used for detecting the touch panel.

The task providing device 103 is a general well-known personal computer. The task providing device 103 displays a task of reverse Stroop interference on the touch panel display 102 connected by a display cable 106, and records information generated by the subject's answering operation on the touch panel display 102.

The brain blood flow measuring device 104 detects, from a head sensor 107 mounted on the subject's head, a signal caused by the brain blood flow, and outputs brain blood flow data to the brain activity recording device 105 connected by a USE cable 108.

The brain activity recording device 105 is also a general well-known personal computer as with the task providing device 103. The brain activity recording device 105 records the brain blood flow data received from the brain blood flow measuring device 104, and also receives and records trigger data such as the start and completion of a task from the task providing device 103 via a LAN cable 109.

The task providing device 103 is realized by installing and executing a program that realizes a function of generating a task of reverse Stroop interference and recording information in a personal computer.

The brain activity recording device 105 is realized by installing and executing a program that realizes a function of recording brain blood flow data and trigger data in a personal computer.

Next, the cognition function testing system 121 illustrated in FIG. 1B will be described.

The cognition function testing system 121 includes the touch panel display 102, a task providing device 123, and the brain blood flow measuring device 104.

The cognition function testing system 121 of FIG. 1B is different from cognitive function testing system 101 of FIG. 1A, and the task providing device 123 serves also as the brain activity recording device 105.

The task providing device 123 is realized by installing and executing both of a program that realizes a function of generating a task of reverse Stroop interference into a personal computer and recording the information, and a program that realizes a function of recording brain blood flow data and trigger data.

Meanwhile, there exist, in addition to the display cable 106, a touch panel cable 110 between the touch panel display 102 and the task providing device 103 or the task providing device 123, as illustrated in both FIGS. 1A and B. There are cases where the touch panel cable 110 may be integrated with the display cable 106, depending on the form of the display cable 106. Specifically, the touch panel cable 110 needs to be a USB cable when the display cable 106 is a display-dedicated cable such as the well-known HDMI, and the touch panel display 102 and the task providing device 103 are connected to the touch panel cable 110. In contrast, when the display cable 106 is a USE cable, the USE cable can be used as the touch panel cable 110 connecting the touch panel display 102 and the task providing device 103.

[Cognitive Function Testing System: Hardware Configuration]

FIG. 2 is a block diagram illustrating a hardware configuration of a personal computer.

A personal computer 201 includes a well-known CPU 202, a ROM 203, a RAM 204, a nonvolatile storage 205 such as a hard disk device, a display section 206, an operation section 307, a real-time clock (RTC) 208 configured to output date and time information, an NIC (Network Interface Card) 209, and a USB interface (USB I/F) 210, all of which is connected to a bus 211.

The task providing device 103 and the brain activity recording device 105 of FIG. 1A, and the task providing device 123 of FIG. 1B function as a task providing device and a brain activity recording device by causing the personal computer 201 to read and execute a predetermined program.

[Cognitive Function Testing System: Functional Configuration]

Figure 3:
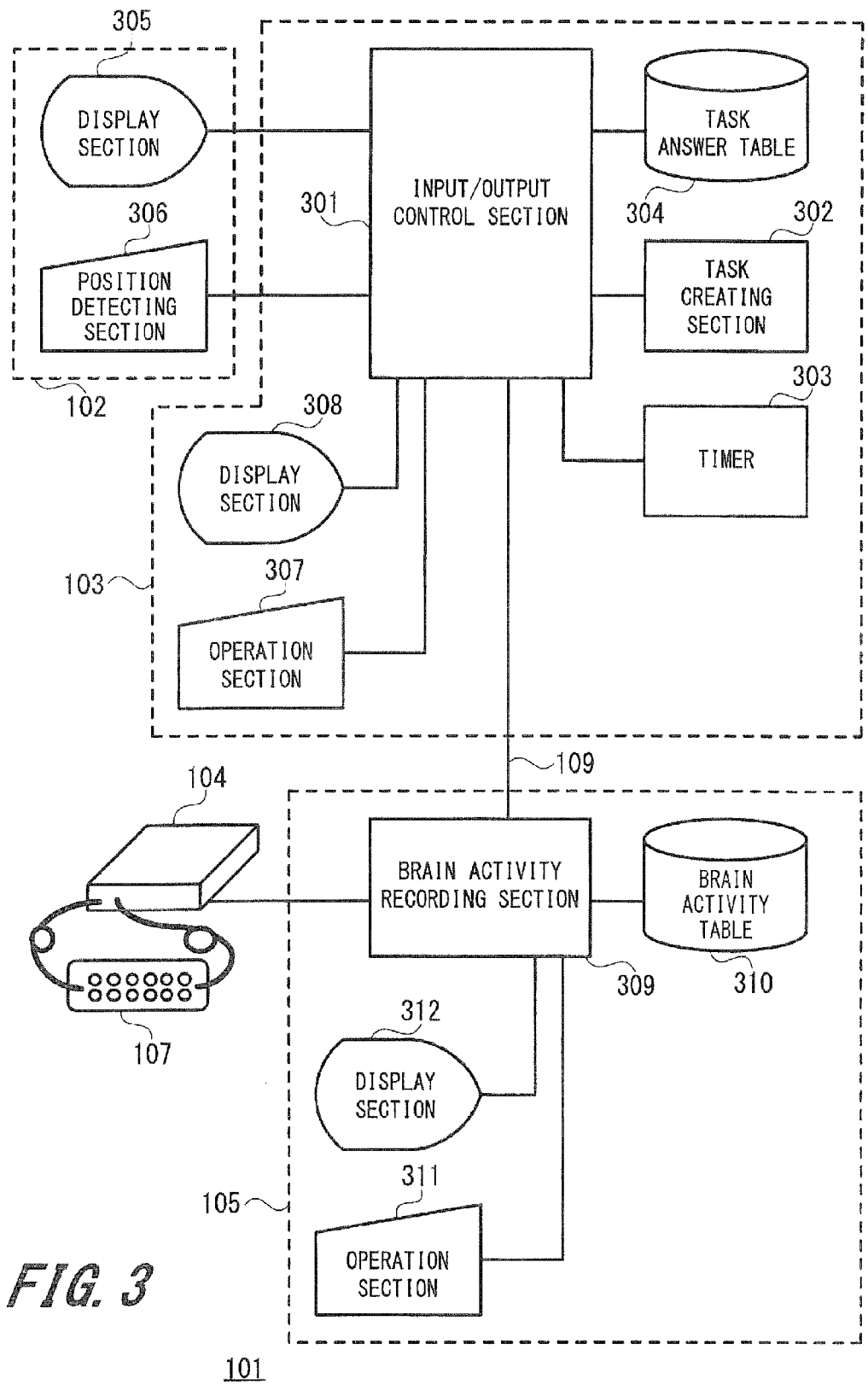
FIG. 3 is a functional block diagram of a cognitive function testing system corresponding to the first example of FIG. 1.
Figure 4:
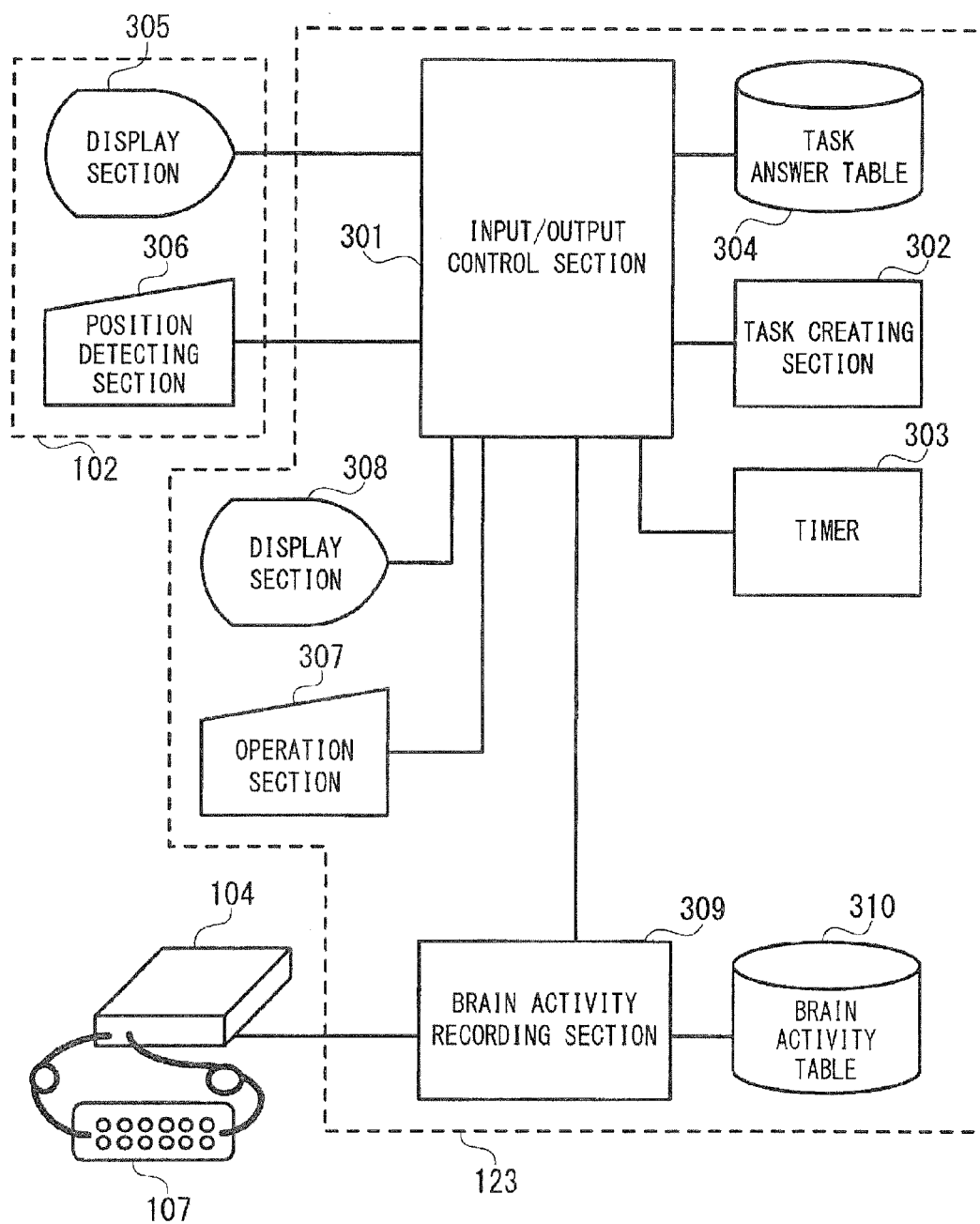
FIG. 4 is a functional block diagram of a cognitive function testing system corresponding to the second example of FIG. 1.

FIGS. 3 and 4 are functional block diagrams of a cognitive function testing system. The functional block diagram of FIG. 3 corresponds to the cognitive function testing system 101 of FIG. 1A, and the functional block diagram of FIG. 4 corresponds to the cognitive function testing system 121 of FIG. 1B, respectively.

First, the cognitive function testing system 101 of FIG. 3 will be described.

The task providing device 103 executes a predetermined program to thereby form therein the input/output control section 301, a task creating section 302, a timer 303, and a task answer table 304, as functions of the task providing device 103.

The task creating section 302 creates a task to be presented to a subject. The input/output control section 301 displays the task created by the task creating section 302 on the display section 305 of the touch panel display 102, and also records, in the task answer table 304 together with the task, coordinate information obtained by the subject's operation of the position detecting section 306 of the touch panel display 102. At this time, the input/output control section 301 obtains timing information from the timer 303, and manages the time period from the time when display of the task started to the time when the subject performs an answering operation, and the time period during which presentation of tasks and recording of answers is continued.

The cognitive function testing system 101 of the present embodiment repeats a 20-second task presentation and answering operation, and a subsequent 10-second break, a predetermined number of times, for example, five times. Hereafter, the total process made up of repetition of the task presentation and answering operation which is followed by a break is referred to as a task sequence. Meanwhile, the 20-second and 10-second time widths, as well as the number of repetition times of five times are merely exemplary, and an appropriate time width and number of times can be set along with accumulation of measurement data.

Upon starting a task sequence in response to the operation of the operation section 307, the task providing device 103 transmits the trigger data indicating that the task sequence has started, to the brain activity recording device 105 through the LAN cable 109. In addition, in the same way, the task providing device 103 transmits different sets of trigger data to the brain activity recording device 105 through the LAN cable 109, respectively, at the start and completion of the 20-second task presentation and answering operation, and at the completion of the task sequence. For example, it is assumed that the start and completion of the task sequence is "6F00" in hexadecimal, the start of a task presentation is "100" in hexadecimal, and the completion of the task presentation is "3300" in hexadecimal.

The trigger data is transmitted using a UDP protocol of the well-known TCP/IP network. As is known, UDP unlike TCP lacks the concept of connection and thus is suitable for transmission and reception, which requires a real-time property, of the trigger data that precisely records the timing indicating the start and completion of an event.

The brain activity recording device 105 executes a predetermined program to thereby form therein a brain activity recording section 309 and a brain activity table 310 as functions of the brain activity recording device 105.

The brain activity recording section 309 receives brain blood flow data from the brain blood flow measuring device 104 in response to the operation of the operation section 311, and also receives the trigger data transmitted from the task providing device 103 through the LAN cable 109 and records it in the brain activity table 310 at a predetermined sampling clock (not illustrated). In the case of the present embodiment, the sampling clock is about 0.66 sec.

A supply source of the sampling clock may be the brain blood flow measuring device 104, or may be the brain activity recording device 105.

Next, the cognition function testing system 121 of FIG. 4 will be described.

The task providing device 123 executes a predetermined program to thereby form therein the input/output control section 301, the task creating section 302, the timer 303, the task answer table 304, the brain activity recording section 309, and the brain activity table 310, as functions of the task providing device 123. Namely, installation and execution of both the program for the task providing device 123 and the program for the brain activity recording device 105 in a single personal computer result in the form of the functional block diagram of FIG. 4. In addition, the fact that the functions provided by the two programs are accommodated in a single personal computer eliminates the need for the LAN cable 109 which has been required for the cognitive function testing system 101 illustrated in FIGS. 1A and 3.

Figure 5:
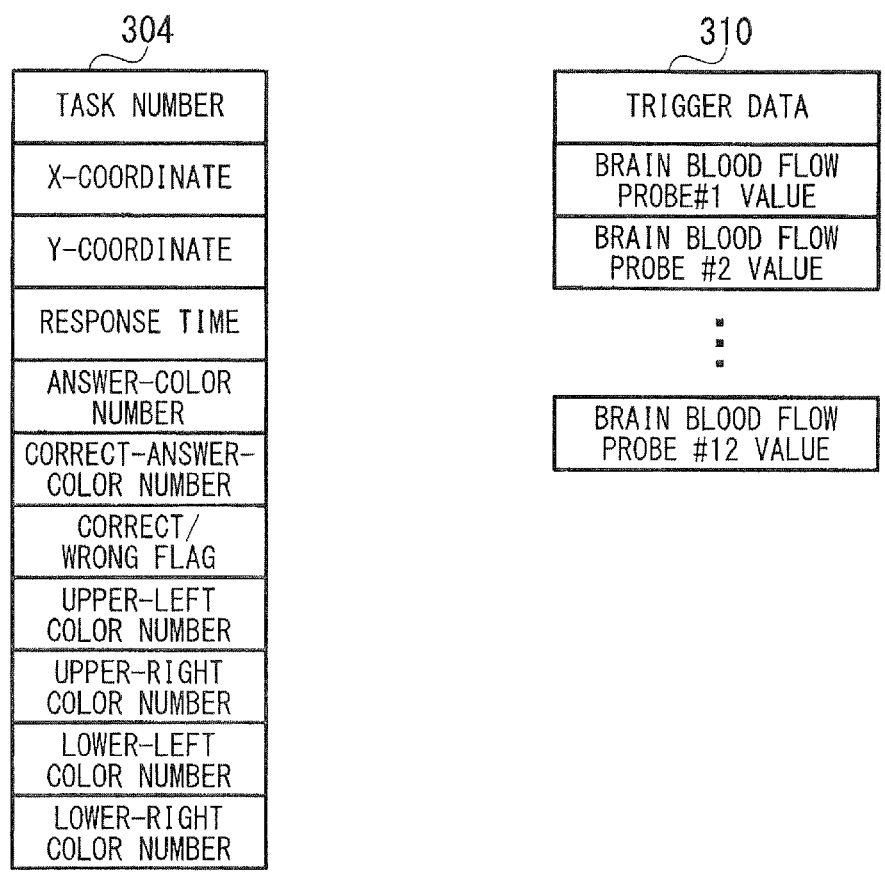
FIG. 5 illustrates a task configuration of a task answer table and a brain activity table.

FIG. 5 illustrates a task configuration of the task answer table 304 and the brain activity table 310.

The task answer table 304 includes a task number field, an X-coordinate field, a Y-coordinate field, a response time field, an answer-color number field, a correct-answer-color number field, a correct/wrong flag field, a upper-left color number field, a upper-right color number field, a lower-left color number field, and a lower-right color number field.

The task number field stores a sequence number provided to a task answered within the 20-second time period of task presentation and answering operation.

The X-coordinate field stores the X-coordinate data of a position of the subject's finger when the subject touches the touch panel display 102.

The Y-coordinate field stores the Y-coordinate data of a position of the subject's finger when the subject touches the touch panel display 102.

The response time field stores the time period, that is, the response time, from the time when a task is displayed on the touch panel display 102 to the time when the subject operates the touch panel display 102. The response time is obtained by the input/output control section 301 referring to the timer 303.

The answer-color number field stores the number of the color displayed on the touch panel display 102, which is derived from the position of the subject's finger when the subject operates the touch panel display 102. For example, the color number "1" corresponding to red is stored when the subject touches with a finger an area where "red" is displayed on the touch panel display 102. In the same way, color numbers corresponding to colors are predetermined by a program of the task providing device 123 as in the case of "2" for "green", "3" for "yellow", and "4" for white. Meanwhile, "0" is stored when an area with no color displayed therein is touched.

The correct-answer-color number field stores the color number corresponding to the correct answer when the subject operates the touch panel display 102.

The correct/wrong flag field stores a flag indicating whether or not the answer is correct when the subject operates the touch panel display 102.

The upper-left color number field, the upper-right color number field, the lower-left color number field, and the lower-right color number field, respectively, store the color numbers of the colors displayed as a task. For example, "1", "2", "4" and "3" are stored in the upper-left color number field, the upper-right color number field, the lower-left color number field, and the lower-right color number field, respectively, when there are displayed "red" on the upper-left, "green" on the upper-right, "white" on the lower-left, and "yellow" on the lower-right.

As described above, the task answer table 304 records clearly therein not only the task presented to the subject, the answer thereto and the response time, but also the X-coordinate and the Y-coordinate when the touch panel display 102 is touched. The coordinate information becomes a big clue in seeking the possibility or tendency of the subject being affected by ADHD or the like.

The brain activity table 310 includes a trigger data field and brain blood flow probe #1 value field to brain blood flow probe #12 value field.

The trigger data field stores the trigger data generated by the input/output control section 301.

The brain blood flow probe fields #1 to #12 respectively store the brain blood flow data obtained from the 12 sensors provided in the head sensor 107.

Meanwhile, the number of fields referred to as "brain blood flow probe" of the brain activity table 310 increases or decreases depending on the number of sensors provided in the head sensor 107.

[Cognitive Function Testing System: Operation]

Figure 6:
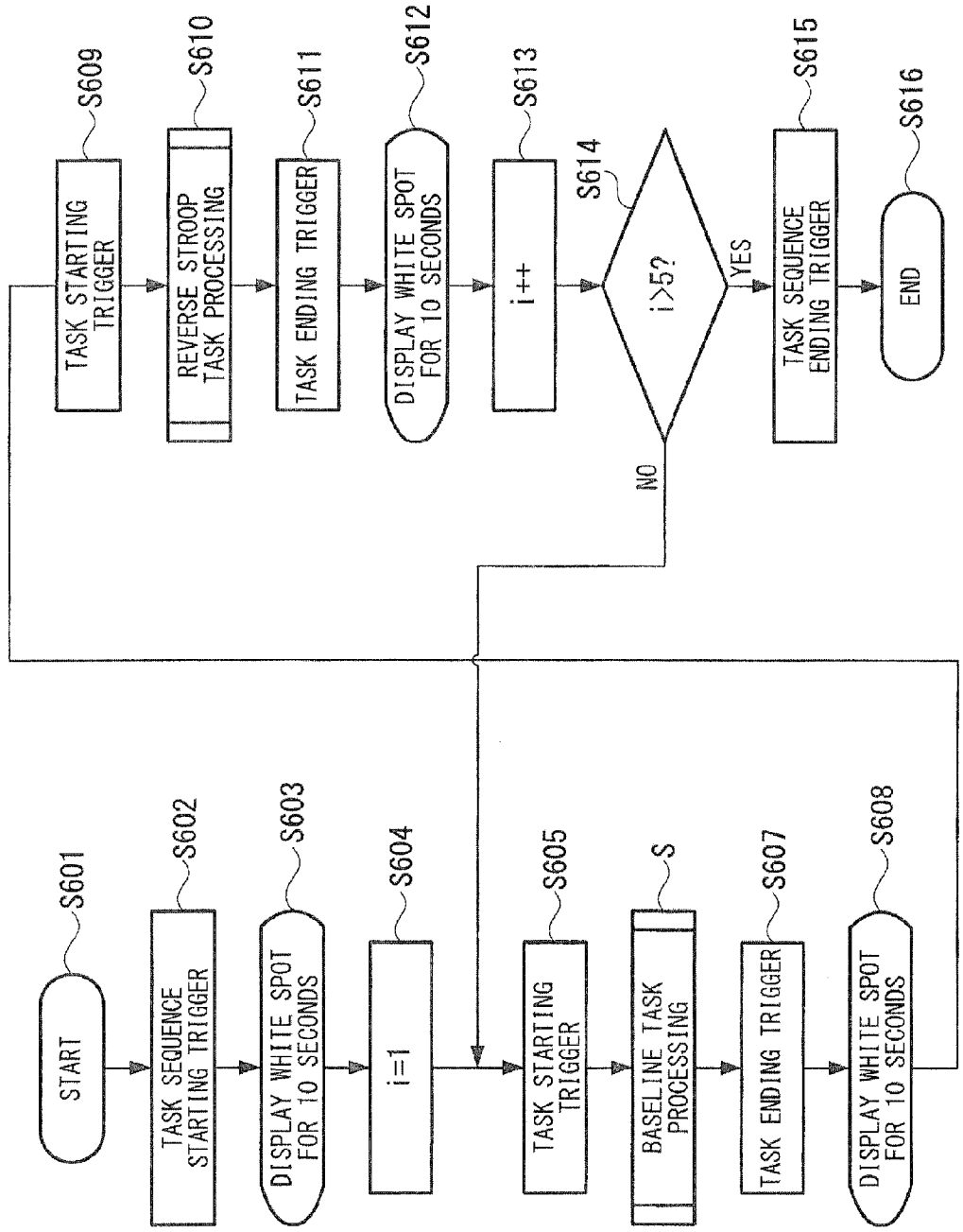
FIG. 6 is a flowchart illustrating the operation flow of a task sequence performed by the cognitive function testing system of the present embodiment.

FIG. 6 is a flowchart illustrating the operation flow of the task sequence performed by the cognitive function testing system 101 of the present embodiment.

When an operator operates the operation section 307 to instruct execution of the task sequence (S601), the input/output control section 301 transmits trigger data "6F00" indicating the start of the task sequence to the brain activity recording section 309 (S602). Subsequently, the input/output control section 301 causes the display section 305 of the touch panel display 102 to display a white spot with a diameter of about 20 to 30 mm at the center of the screen for 10 seconds (S603). The time period is provided for stabilizing the brain activity of the subject. The manner of displaying the white spot is similar to that at steps S608 and S612 described below.

Next, the input/output control section 301 provides a counter variable i in the inside (not illustrated) and initializes its value to "1" (S604). Meanwhile, steps S602 to S604 may be performed in any order.

Next, the input/output control section 301 transmits trigger data "100" indicating the start of a task to the brain activity recording section 309 (S605). Subsequently, the input/output control section 301 controls the task creating section 302 to thereby perform a baseline task processing for 20 seconds (S606). A baseline task is "a task of requesting to answer the same color as the meaning or color of the word when the meaning of the word displayed on the screen is the same as the color of the word".

When the baseline task processing is finished, the input/output control section 301 transmits trigger data "3300" indicating the completion of the task to the brain activity recording section 309 (S607). Subsequently, the input/output control section 301 causes the display section 305 of the touch panel display 102 to display a white spot of a diameter of about 20 to 30 mm at the center of the screen for only 10 seconds, in the same way as in step S603 (S608).

Next, the input/output control section 301 transmits trigger data "100" indicating the start of a task to the brain activity recording section 309 (S605). Subsequently, the input/output control section 301 controls the task creating section 302 to execute the reverse Stroop task processing for only 20 seconds (S606). A reverse Stroop task is "a task of requesting to answer the same color as the meaning of the word when the meaning of the word displayed on the screen is different from the color of the word".

When the reverse Stroop task processing is finished, the input/output control section 301 transmits trigger data "3300" indicating the completion of the task to the brain activity recording section 309 (S611).

Next, the input/output control section 301 increments a counter variable i by 1 (denoted as "i++" in FIG. 6) (S613), and checks whether or not the counter variable i exceeded a threshold value "5" (S614).

When the counter variable i is equal to or less than 5 (NO at S614), the input/output control section 301 repeats the processing from step S605 again.

When the counter variable i exceeds 5 (YES at S614), the input/output control section 301 transmits trigger data "6F00" indicating the completion of the task sequence to the brain activity recording section 309 (S615), and terminates a series of the processing (S616).

Figure 7:
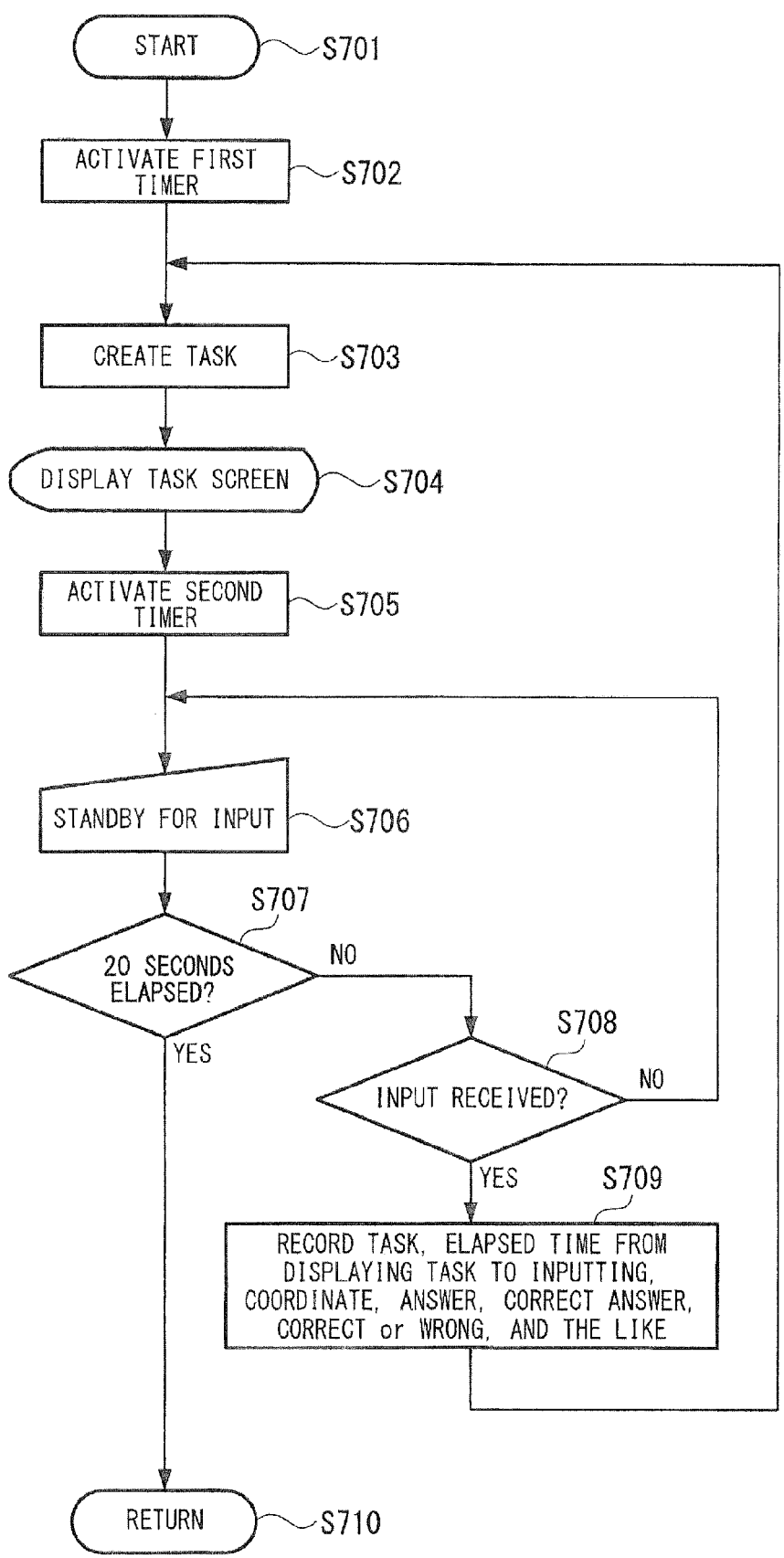
FIG. 7 is a flowchart illustrating a flow of baseline task processing and reverse Stroop task processing.

FIG. 7 is a flowchart illustrating flow of the baseline task processing and the reverse Stroop task processing. The flowchart of FIG. 7 illustrates the details of the processing of steps S606 and S610 of FIG. 6. The processing flows of step S606 which is the baseline task processing and step S610 which is the reverse Stroop task processing are exactly the same except for the difference of the type of the task to be presented, the description will be given in the same flowchart.

Upon starting the processing (S701), the input/output control section 301 first activates a first timer (S702).

Next, the input/output control section 301 causes the task creating section 302 to create a task (S703). At this time, in the case of the baseline task processing of step S606, the input/output control section 301 causes the task creating section 302 to create a baseline task. In addition, In the case of the reverse Stroop task processing of step S610, the input/output control section 301 causes the task creating section 302 to create a reverse Stroop task. In addition, the input/output control section 301 displays the task data created by the task creating section 302 on the display section 305 of the touch panel display 102 (S704). Next, the input/output control section 301 activates a second timer (S705), and waits for an input operation of the position detecting section 306 of the touch panel display 102 (S705).

The input standby at step S706 is repeated until the first timer has clocked 20 seconds (S707). When 20 seconds have not passed from step S702 (NO at S707), the input/output control section 301 checks whether or not there has been an input operation from the position detecting section 306 of the touch panel display 102 (S708).

When there has been no input operation on the position detecting section 306 (NO at S708), the input/output control section 301 repeats the processing from step S706 again.

When there is an input operation on the position detecting section 306 (YES at S708), the input/output control section 301 records, in the task answer table 304, (S709):
- the task information created by the task creating section 302 at step S703;
- the timed clocked by the second timer, that is, the elapsed time from a time when the task is displayed on the display section 305 at step S704 to a time when the subject performs an input operation on the position detecting section 306;
- the coordinate information output by the position detecting section 306 based on the subject's operation;
- the answer information indicated by the subject's operation;
- the correct answer information for the task of step S703; and
- the correct/wrong flag indicating whether or not the subject has answered the task of step S703 correctly.

In addition, the input/output control section 301 repeats the processing from step S703 again.

When the first timer has clocked 20 seconds at step S707 (YES at S707), the series of processing is terminated (S710).

The operation illustrated in the flowchart of FIG. 7 indicates that the subject performs the baseline task or reverse Stroop task within 20 seconds. When the subject touches the touch panel display 102 in order to perform an answering operation, the next task is displayed at the moment of touching, regardless of whether the answer is correct or wrong. Therefore, the faster the subject's answer speed, the more tasks the subject can answer.

[Cognitive Function Testing System: Example of Screen Display]

Figure 9C:
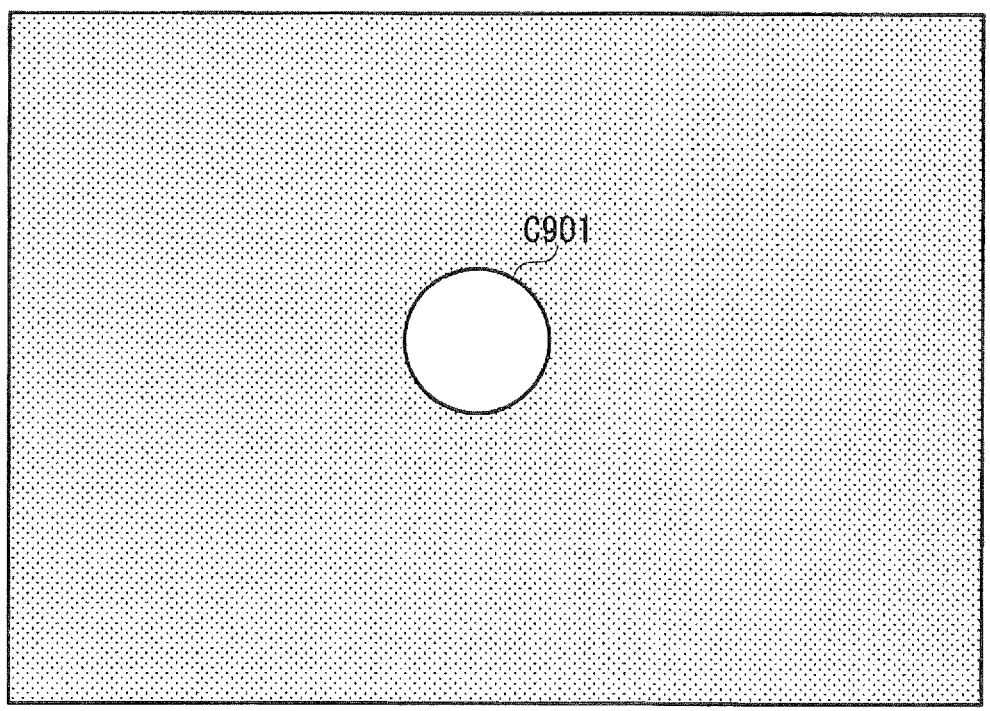
FIG. 9 is another exemplary display screen displayed on the touch panel display by the cognitive function testing system of the present embodiment.

FIGS. 8A, 8B and 9C are examples of the display screen displayed on the touch panel display 102 by the cognitive function testing system 101 of the present embodiment. All the display screens illustrated in FIGS. 8A, 8B and 9C have black backgrounds.

FIG. 8A is an exemplary display screen of a baseline task.

A quadrangular tile T801 on the upper-left of the screen is "red" colored, a quadrangular tile T802 on the upper-right of the screen is "green" colored, a quadrangular tile T803 on the lower-left of a screen is "yellow" colored, and a quadrangular tile T804 on the lower-right of the screen is "white" colored. A word C805 "red" is displayed at the center in red color. In this case, a correct answer results when touching the tile T801 on the upper-left of the screen, whereas a wrong answer results when touching other tiles or anywhere other than the tiles.

FIG. 8B is an exemplary display screen of a reverse Stroop task.

A quadrangular tile T811 on the upper-left of the screen is colored "yellow", a quadrangular tile T812 on the upper-right of the screen is "red" colored, a quadrangular tile T813 on the lower-left of the screen is "white" colored, and a quadrangular tile T814 on the lower-right of the screen is "green" colored. A word "red" C815 is displayed at the center in white color. In this case, a correct answer results when touching the tile T812 on the upper-right of the screen having the same "red" color as the meaning of the word, whereas a wrong answer results when touching other the tiles or anywhere other than the tiles.

The task creating section 302 creates screens such as those illustrated in FIGS. 8A and 8B, by making the combination of tile colors, word colors and word contents different at random.

FIG. 9C is an exemplary display screen before starting a task and during a break just after the completion of the task.

A white circle C901 is drawn at the center of the black background. The brain activity of the subject is stabilized by displaying the screen for 10 seconds to thereby allow the subject to rest.

The above-described cognitive function testing system 101 has the following outstanding features.

(1) Unlike the conventional paper-based Stroop interference test, one task is displayed on one screen. Since, in the case of the paper-based Stroop interference test, a plurality of tasks is printed on a sheet of paper in a listed manner, interference among other tasks may act, whereby there seems to exist a disadvantage of a higher rate of wrong answers given even by a normal person. The cognition function testing system 101 of the present embodiment is expected to provide a more correct testing of the cognitive function since there can be essentially no interference among other tasks.

(2) Unlike the paper-based Stroop interference test, it is possible to measure the required time period, that is, the response time, from a time when a task is displayed on the touch panel display 102 to a time when the subject performs an answering operation. Change in the fatigue degree, concentration of the brain and the like can be estimated by observing the response time.

(3) Unlike the paper-based Stroop interference test, the coordinate information when the subject operates the touch panel display 102 is also recorded. The tendency of answering operations can be observed from the coordinate information such as how the subject has made wrong answers.

(4) Unlike the paper-based Stroop interference test, the brain blood flow data of the subject is also recorded. Furthermore, the brain blood flow data can be synchronized with the task answer table 304 by using the trigger data. Namely, correlation of the tendency of correct and wrong answers with the brain blood flow data can be observed.

ADHD is diagnosed on the basis of three symptoms: carelessness, hyperactivity, and impulsiveness. However, it is difficult to objectively quantify such symptoms, and thus a clinical diagnosis of the disease becomes difficult.

Various approaches for quantifying such symptoms have been devised up to the present time and several testing methods are currently being available for clinical application. However, all such testing methods are also based on a simple operation during a certain time period of clicking on a key each time a target stimulus is displayed on the screen, and only measurements of the response time, wrong response, or absence of response allow quantification, and thus the testing methods are insufficient as an objective index for clinical diagnosis.

According to the present invention, not only the measurements of the response time, wrong response, or absence of response to the target stimulus but also the use of the touch panel display makes it possible to record, in the task answer table, the coordinate information when the subject performs an answering operation, and thus the core symptom of ADHD can be quantified in detail.

Although precise pointing to the target stimulus in the present task is possible by suppressing interference of colors or meanings when the subject is a normal child or adult, in the case of a child or an adult with developmental disorder represented by ADHD, there occurs a tendency such as pointing by deviation from the target stimulus due to disorder of concentration or suppression function. The analysis of the recorded coordinate information makes it possible to quantify the degree of such deviation, that is, the core symptoms of ADHD. Particularly, the analysis of how far the pointed coordinate is separated from the target stimulus allows measurement of impulsivity which is one of the core symptoms of ADHD, and the analysis of the variation of the distance between the pointed coordinate and the target stimulus allows measurement of variability of attention, which provides a strong index when performing clinical diagnoses of such diseases.

Furthermore, since the coordinate information is accumulated as data, the more the subject data is collected by operating the cognitive function testing system of the present embodiment, the more detailed and precise grasp of the causal relation between the tendency of variation of the coordinate information and impulsivity become possible.

Moreover, there are many documents of conventional studies on examination of brain activity with ADHD, reporting that the activity of the prefrontal cortex of children with ADHD is lower than that of normal children. Since it is known that the activity of the prefrontal cortex related to high-level cognition which requires suppression function or the like is lower in the case of children with ADHD than in the case of normal children performing a task, the measurement of the brain activity while performing a task may be an objective index for clinical diagnosis of children with ADHD.

The operation of the cognitive function testing system of the present embodiment causes the possibility of obtaining completely new findings such as correlation among the task given to the subject, change of the brain activity of the subject, and the degree of the coordinate information being disturbed. Accordingly, it is extremely useful to record data during the execution of a task together with information such as the trigger data, the information serving as an index incorporating the chronological order.

[Cognitive Function Estimation System: Clinical Test Result]

Hereinafter, a cognitive function estimation system according to the second embodiment of the present invention will be described.

The inventors have performed testing on typically developed children (normal children), ASD (Autistic Spectrum Disorder) children, and ADHD children through the use of the cognitive function testing system according to the first embodiment of the present invention.

FIG. 10 is a table indicating the result of the test performed by the cognitive function testing system on a plurality of typically developed children, ASD children, and ADHD children.

In FIG. 10, "TDC" refers to a Typically Developed Child. In addition, an interference rate is a value calculated by the following formula:

Interference rate=(number of correct answers to non-interference test−number of correct answers to interference test)/number of correct answers to non-interference test×100

The number of correct answers to non-interference test is the number of correct answers in a baseline task.

The number of correct answers to interference test is the number of the correct answers in a Stroop task or a reverse Stroop task.

First, it can be seen that the interference rate for ADHD children in a reverse Stroop task of FIG. 10 is significantly higher than the values of TDC and ASD children.

Next, it can be seen that the number of wrong answers by ADHD children in the reverse Stroop task of FIG. 10 is significantly higher than the values of TDC and ASD children.

Furthermore, it can be seen that the correct answer rate by ADHD children in the reverse Stroop task of FIG. 10 is significantly lower than the values of TDC and ASD children.

Figure 11:
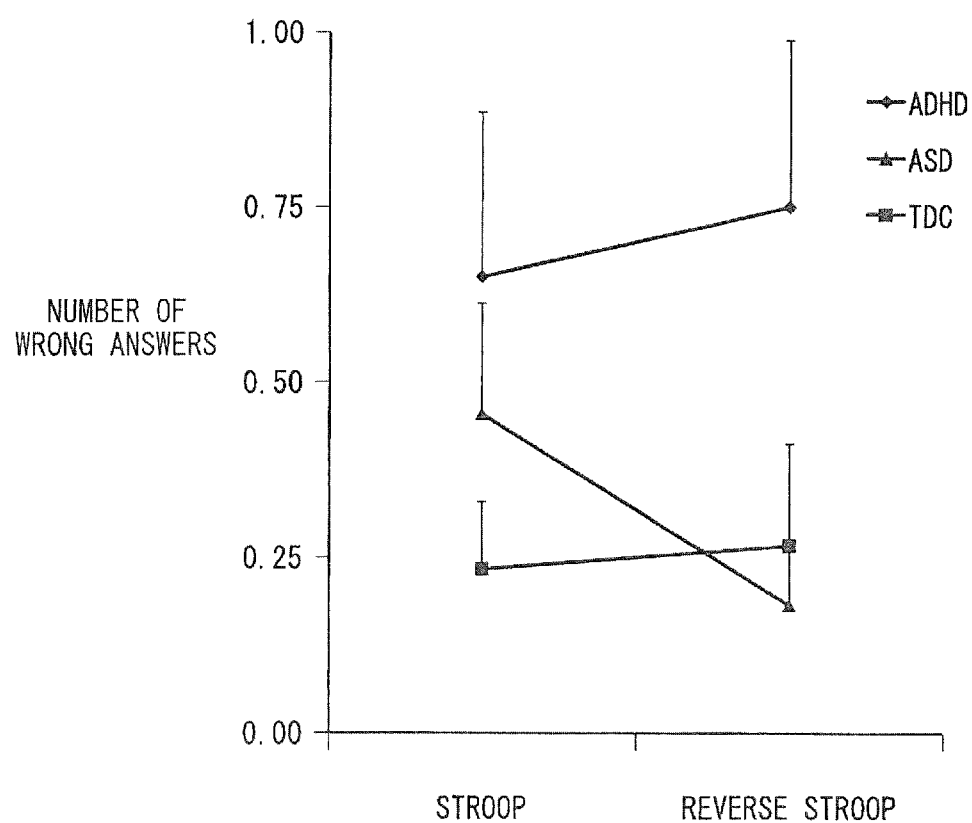
FIG. 11 is a graph indicating the number of wrong answers to a Stroop task and a reverse Stroop task, as a result of the test performed by the cognitive function testing system on a group of typically developed children, ASD children, and ADHD children.

FIG. 11 is a graph indicating the number of interference errors in the Stroop task and the reverse Stroop task, as a result of the test performed by the cognitive function testing system on a plurality of typically developed children, ASD children, and ADHD children.

It can be seen that the gradient of the graph for ADHD children of FIG. 11 is significantly steeper in the increasing direction than the gradient of the graphs for TDC and ASD children. Namely, it can be clearly seen that ADHD children are worse at reverse Stroop tasks than Stroop tasks in comparison with other children.

Moreover, it can also be seen that performing only Stroop tasks is not appropriate for diagnosis of ADHD.

Figure 12B:
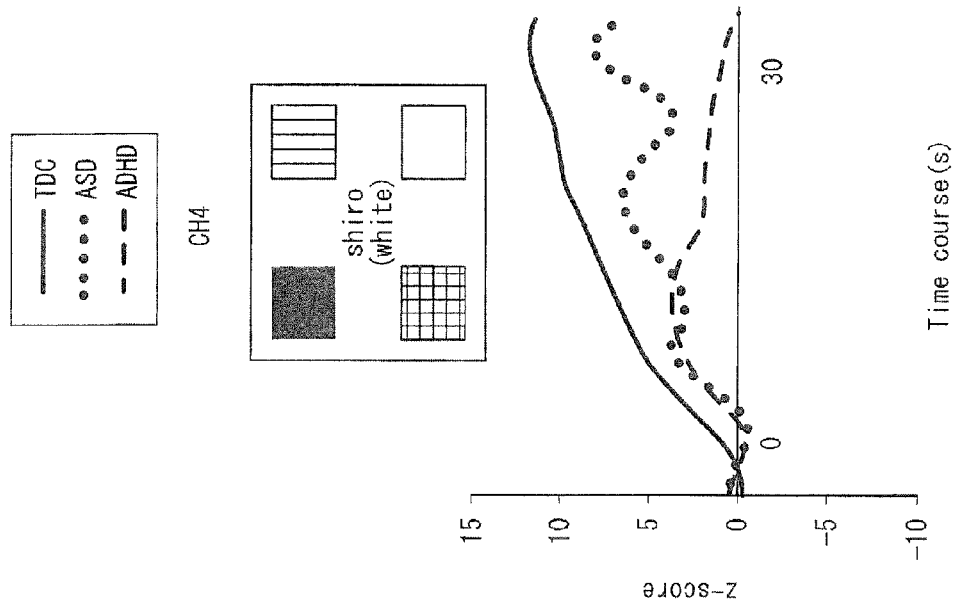
FIG. 12 is a graph of averaged numerical values of the brain blood flow in the right side of the forehead of a subject when solving a Stroop task and a reverse Stroop task.
Figure 12A:
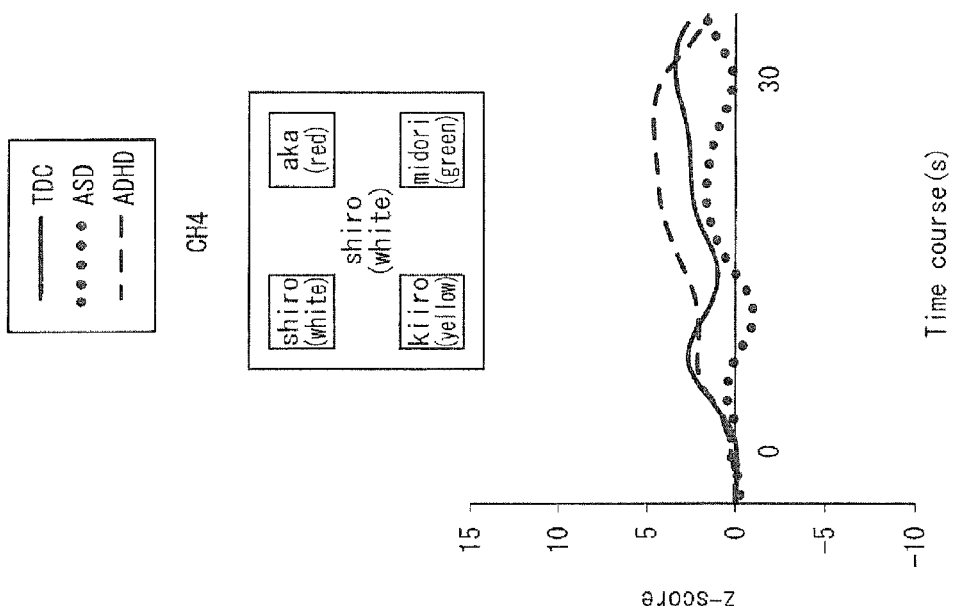

FIGS. 12A and 12B are graphs of averaged numerical values of the brain blood flow on the right side of the forehead when solving a Stroop task and a reverse Stroop task.

FIG. 12A is a graph of averaged numerical values of the brain blood flow on the right outside prefrontal cortex when solving the Stroop task. No significant difference can be seen among all the children.

FIG. 12B is a graph of averaged numerical values of the brain blood flow in the right outside prefrontal cortex when solving the reverse Stroop task.

It can be seen that the brain blood flow of typically developed children clearly increases over time.

It can be seen that the brain blood flow of ASD children tends to increase over time, although being unstable.

It can also be seen that the brain blood flow of ADHD children tends to clearly decrease over time, from the middle of the task.

[Cognitive Function Estimation System: Application of Cognitive Function Testing System]

From the above test results, it can be considered possible to estimate the degree of the subject's cognitive function by performing Stroop tasks and reverse Stroop tasks through the use of the cognitive function testing system according to the present embodiment and by observing the interference rate of the reverse Stroop tasks and the ratio between the number of wrong answers to the Stroop tasks and the reverse Stroop tasks. Furthermore, it can be considered possible to estimate the degree of the subject's cognitive function by measuring the brain blood flow and by observing the change of the brain blood flow in performing the Stroop tasks and the reverse Stroop tasks.

Therefore, the "cognitive function estimation system" can be realized by including, in the input/output control section 301 of the cognition function testing systems 101 and 121 according to the first embodiment, a calculation processing function of estimating the cognitive function and a function of displaying the result of calculation on the display section 308.

The calculation processing of estimating the cognitive function makes use of a learning algorithm such as Bayesian estimation or a support vector machine, which are well-known as spam email filter and the like. In the specific calculation processing, answer results and brain blood flow measurement data of many subjects have been preliminarily taught by the predetermined learning algorithm. Next, the answer data and the brain blood flow measurement data are obtained by solving a task by a subject. In addition, the answer data and the brain blood flow measurement data are verified by the learning algorithm to thereby convert the level of the cognitive function into an appropriate numerical value and present the value to the user through the display section 308. The result of estimation is displayed with a quantified probability, such as "probability of having ADHD is XX %", for example.

Meanwhile, the functional block diagram of the cognitive function estimation system according to the second embodiment is exactly the same as those of FIGS. 2 and 3, and thus description thereof will be omitted.

The following applications are conceivable in the present embodiment.

(1) Although the task creating section 302 presents reverse Stroop tasks in the cognitive function testing system 101 of the present embodiment, Stroop tasks may be presented instead of reverse Stroop tasks. A Stroop task is "a task of requesting to answer the same color as the color of the word when the meaning of the word displayed on the screen is different from the color of the word".

In addition, Stroop tasks and reverse Stroop tasks may be alternately presented.

(2) Although the touch panel display 102 is rectangular and thus the number of colors displayed in a task is four in the cognitive function testing system 101 of the present embodiment, the number of colors displayed in a task is not necessarily limited to four.

FIGS. 13A and 13B are examples of a display screen in the case of five colors.

It is also possible to display colors in equally divided segments by using a regular pentagon illustrated in FIG. 13A or a circle illustrated in FIG. 13B.

In the same way, one-sixth segments of a regular hexagon or a circle for six colors, and one-seventh segments of a regular heptagon or a circle can be used in the case of seven colors, respectively.

Namely, a task using more than four colors can be created by causing the touch panel display 102 to display equally divided segments of a regular polygon or a circle in accordance with the number of colors.

Meanwhile, when there will be five or more choices, it is also conceivable to reduce the subject's burden such as reduction in the execution time of a task from 20 seconds to 15 seconds, or increase in the 10-second break time to 15 seconds.

(3) When studying diseases such as ADHD, it is also important to observe the characteristics of the behavior of the patient who is the subject, in addition to collecting the content of answers and data of the brain blood flow which can be observed by the cognitive function testing system 101 of the present embodiment. Therefore, it is considered that the subject solving a task sequence is photographed through the use of a video camera. Photographing the subject with a commercial video camera allows observation of the characteristics of his behavior. However, simply photographing cannot chronologically synchronize the data. In the case of the brain activity table 310, trigger data is recorded in the brain activity table 310 to allow chronological synchronization between the task answer table 304 and the brain activity table 310, but inmost cases commercial video cameras are not provided with a channel for recording trigger data.

Therefore, a video camera includes in the object a video image that works as a trigger, instead of recording the trigger data.

FIG. 14 is a schematic view illustrating a scene of photographing the subject and the cognitive function testing system using a video camera.

Figure 15:
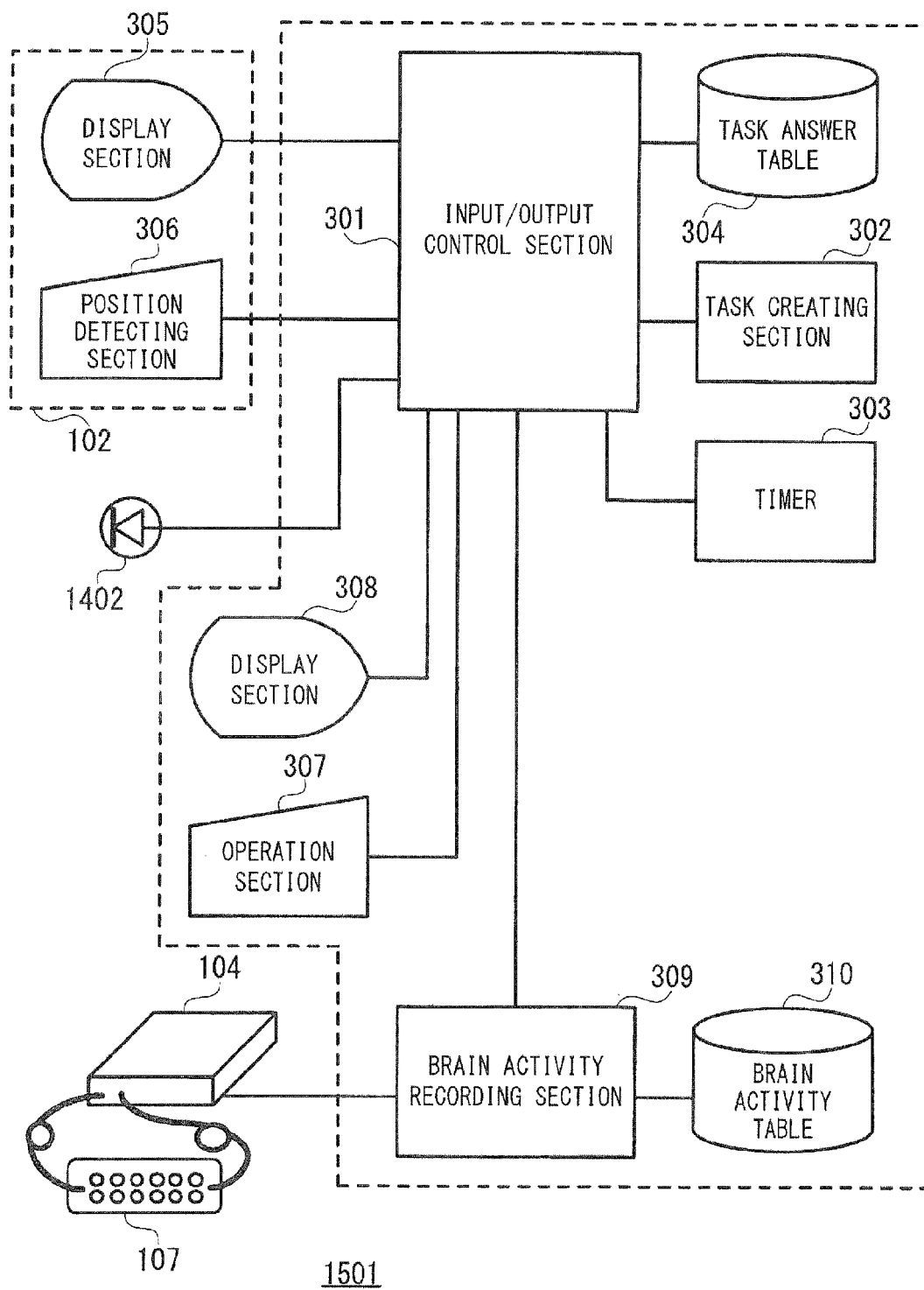
FIG. 15 is a functional block diagram of the cognitive function testing system in the application of photographing the subject and the cognitive function testing system by using a video camera.

FIG. 15 is a functional block diagram of the cognitive function testing system in the application.

The cognition function testing system 1501 illustrated in FIG. 15 has almost the same functional configuration as the cognitive function testing system 121 of FIG. 4, and only differs in that an infrared LED 1402 is connected to the input/output control section 301. It goes without saying that the cognitive function testing system 101 of FIG. 3 may be provided with the infrared LED 1402 as with FIG. 15.

As illustrated in FIG. 14, a subject 1401, with the head sensor 107 wound around his head, operates the touch panel display 102. A video camera 1403 films the subject 1401.

At this time, the infrared LED 1402 is adhesively bonded on the back side of the touch panel display 102, and the infrared LED 1402 is controlled by the task providing device 103 to emit light at the same timing as the trigger data.

As is known, the light emitted by the infrared LED 1402 is invisible to human eyes. However, a CCD imaging element or a CMOS imaging element used for the video camera 1403 is capable of capturing the light emission by the infrared LED 1402 and outputting it as video signals.

The infrared LED 1402 emits light on the basis of the control by the input/output control section 301, as illustrated in FIG. 15.

In such a manner, the light emission by the infrared LED 1402 is recorded in the video data captured by the video camera 1403 which is not electrically connected to the cognitive function testing system 101, and thus the task answer table 304 and the brain activity table 310 can be chronologically synchronized with the aid of light emission by the infrared LED 1402.

(4) The cognitive function testing system 101 of the present embodiment may also be formed by an electromagnetic touch panel display 102. In such a case, a dedicated position indicator having a built-in circuit including a coil may be used instead of a finger to operate the touch panel display 102.

(5) Instead of recording the brain blood flow data, brain waves may be recorded. Namely, it suffices that the brain activity data collecting means connected to the brain activity recording device 105 is a device that outputs data derived from brain activity of the cerebral cortex.

(6) The following may be conceivable as a variation of the baseline task:
  a display form of changing the color of the word displayed at the center of the screen of the touch panel display 102 to a monochromatic color such as black; or
  a display form of changing the word displayed at the center of the screen of the touch panel display 102 to a color patch (colored square). It is considered that the variations make the baseline tasks effective in checking the degree inherent to color interference, or the degree inherent to meaning interference.

(7) The following may be conceivable as a variation of the baseline task and the reverse Stroop task:
  a display form of replacing the color-segmented tiles displayed at the four corners of the screen of the touch panel display 102 with a color-segmented word;
  a display form of using shapes such as "*(star)", "• (circle)" or the like, instead of the word displayed at the center of the screen of the touch panel display 102, or the color-segmented tiles displayed at the four corners, to thereby make a choice of shapes avoiding interference of corresponding colors and meanings. Although the well-known Stroop interference and reverse Stroop interference are tasks that make use of the discrepancy between the color and meaning of a word, the use of the "symbol" instead of "color" may also be an effective means of examining the Stroop interfere and reverse Stroop interference.

(8) It is also possible to examine the tendency of the disease of a subject by causing the subject to make a verbal answer instead of operating the touch panel display 102, and by recording the answer. Meanwhile, in such a case, since information indicating the start and completion of a task is included in the recorded data, it is desirable to use voice guidance corresponding to the trigger data together.

(9) According to the statistical result illustrated in FIGS. 10 and 11, it has become clear that the estimation of the possibility of having a disorder such as ADHD is possible without the brain blood flow data. Therefore, although it is desired that the cognitive function testing system and the cognitive function estimation system measure the brain blood flow and record the brain blood flow data, together with answer data of the reverse Stroop task, the brain blood flow data is not always necessary. Namely, the cognitive function testing system and the cognitive function estimation system can be established without the brain blood flow measuring device 104 in FIG. 1.

A cognitive function testing system has been disclosed in the present embodiment.

Unlike the conventional paper-based Stroop interference test, the cognitive function testing system displays one task on one screen and records, in the task answer table 304, not only the subject's correct or wrong answer to a task but also the coordinate information when the subject performs an answering operation on the touch panel display 102. Accordingly, the tendency of the subject's answers can be collected in the form of data, whereby there can be provided data very useful for analyzing and considering various data for various psychiatric disorder besides ADHD.

Furthermore, a cognitive function estimation system has been disclosed in the present embodiment.

The addition of a learning-algorithm-based estimation processing function to the cognitive function testing system according to the first embodiment makes it possible to estimate the level of the cognitive function of the subject. Meanwhile, estimation of the cognitive function can be sufficiently achieved with only the data of answers to the tasks. In addition, it is expected that the addition of the measurement data of the brain blood flow further improves the estimation precision of the cognitive function.

Although exemplary embodiments of the present invention have described above, the present invention is not limited to the aforementioned exemplary embodiments and includes other exemplary variations or applications provided that they do not deviate from the spirit of the present invention described in the appended claims.

For example, the aforementioned exemplary embodiments describe the configuration of the device and the system in detail and specifically in order to provide a comprehensive explanation of the present invention and do not necessarily have all the described components. In addition, it is possible to replace a part of the components of a certain working example by components of another working example, and further possible to add components of another working example to the components of a certain working example. Furthermore, a part of the components of each working example may be deleted, added or replaced by other components.

Moreover, apart or all of the aforementioned components, functions, processing sections or the like may be realized by hardware designed on the basis of integrated circuits, for example. In addition, a part or all of the aforementioned components, functions or the like may be realized by software by which a processor interprets and executes programs that realize respective functions. Information of programs, tables, files or the like that realize respective functions may be stored in a volatile or a nonvolatile storage such as a memory, a hard disk, an SSD (Solid State Drive), or a recording medium such as an IC card, an optical disk or the like.

Furthermore, control lines and information lines are illustrated as necessary and therefore not all the control lines and information lines of a product are illustrated. Actually, it may be assumed that almost all the components are connected to each other.

REFERENCE SIGNS LIST

101: cognitive function testing system, 102: touch panel display, 103: task providing device, 104: brain blood flow measuring device, 105: brain activity recording device, 106: display cable, 107: head sensor, 108: USB cable, 109: LAN cable, 110: touch panel cable, 121: cognitive function testing system, 123: task providing device, 201: personal computer, 202: CPU, 203: ROM, 204: RAM, 205: nonvolatile storage, 206: display section, 208: real-time clock, 209: NIC, 210: USB interface, 211: bus, 301: input/output control section, 302: task creating section, 303: timer, 304: task answer table, 305: display section, 306: position detecting section, 307: operation section, 308: display section, 309: brain activity recording section, 310: brain activity table, 311: operation section, 1401: subject, 1402: infrared LED, 1403: video camera, 1501: cognitive function testing system

The invention claimed is:

1. A cognitive function testing system comprising:
   a display section capable of displaying a plurality of colors;
   a position detecting section configured to output coordinate information of a position touched with a subject's finger or a position indicator used by the subject, and configured to form a touch panel display by being combined with the display section;
   a task creating section configured to create a task including tiles of a plurality of colors and words indicating colors, for being displayed on the display section;
   a task answer table recording the task and the coordinate information; and
   an input/output control section configured to display the task on the display section and record the task and the coordinate information in the task answer table.

2. The cognitive function testing system according to claim 1, further comprising:
   a timer configured to measure elapsed time,
   wherein
   the input/output control section records, in the task answer table, a response time from a time when the task is displayed on the display section by using the timer to a time when the position detecting section is operated.

3. The cognitive function testing system according to claim 2, further comprising:
   a brain activity table recording data derived from brain activity of the subject; and
   a brain activity recording section configured to record, in the brain activity table by a predetermined sampling clock, the data derived from brain activity of the subject and trigger data generated by the input/output control section at a predetermined timing.

4. A cognitive function estimation system comprising:
   a display section capable of displaying a plurality of colors;
   a position detecting section configured to output coordinate information of a position touched with a subject's finger or a position indicator used by the subject, and configured to form a touch panel display by being combined with the display section;
   a task creating section configured to create a task including tiles of a plurality of colors and words indicating colors, for being displayed on the display section;
   a task answer table recording the task and the coordinate information; and
   an input/output control section configured to display the task on the display section, record the task and the coordinate information in the task answer table, and estimate the cognitive function of the subject on the basis of the task and the coordinate information recorded in the task answer table.

5. The cognitive function estimation system according to claim 4, further comprising:
   a timer configured to measure elapsed time,
   wherein
   the input/output control section records, in the task answer table, a response time from a time when the task is displayed on the display section by using the timer to a time when the position detecting section is operated.

6. The cognitive function estimation system according to claim 4, further comprising:
   a brain activity table recording data derived from brain activity of the subject; and
   a brain activity recording section configured to record, in the brain activity table by a predetermined sampling clock, the data derived from brain activity of the subject and trigger data generated by the input/output control section at a predetermined timing,
   wherein
   the input/output control section estimates the cognitive function of the subject on the basis of data derived from brain activity of the subject and recorded on the brain activity table.

7. A cognitive function testing method comprising:
   a task displaying step of creating a task including tiles of a plurality of colors and words indicating colors, and displaying the task on a display section capable of displaying a plurality of colors;
   an answer recording step of outputting coordinate information of a position touched with a subject's finger or a position indicator used by the subject, and recording, in a task answer table together with the task, the coordinate information obtained from a position detecting section that forms a touch panel display by being combined with the display section; and
   a repeating step of repeating the task displaying step and the answer recording step during a predetermined time period.

8. The cognitive function testing method according to claim 7, wherein
   the answer recording step also records, in the task answer table, the elapsed time from a time when the task is displayed on the display section at the task displaying step to a time when the coordinate information is obtained from the position detecting section.

9. The cognitive function testing method according to claim 8, further comprising:
   a brain activity recording step of recording data derived from brain activity of the subject in the brain activity table while the repeating step is being performed.

10. A cognitive function estimation method comprising:
    a task displaying step of creating a task including tiles of a plurality of colors and words indicating colors, and displaying the task on a display section capable of displaying a plurality of colors;
    an answer recording step of outputting coordinate information of a position touched with a subject's finger or a position indicator used by the subject, and recording, in a task answer table together with the task, the coordinate information obtained from a position detecting section that forms a touch panel display by being combined with the display section;
    a repeating step of repeating the task displaying step and the answer recording step during a predetermined time period; and
    a cognitive function estimating step of estimating the cognitive function of the subject on the basis of the task and the coordinate information, recorded in the task answer table.

11. The cognitive function estimation method according to claim 9, wherein
    the answer recording step also records, in the task answer table, the elapsed time from a time when the task is displayed on the display section at the task displaying step to a time when the coordinate information is obtained from the position detecting section.

12. The cognitive function estimation method according to claim 11, further comprising:

a brain activity recording step of recording data derived from brain activity of the subject in the brain activity table while the repeating step is being performed,
wherein
the cognitive function estimating step also uses data derived from brain activity of the subject and recorded in the brain activity table, for an estimation calculation of the cognitive function.

\* \* \* \* \*